United States Patent [19]
Biedermann et al.

[11] Patent Number: 6,156,071
[45] Date of Patent: Dec. 5, 2000

[54] TUBULAR FABRIC AND METHOD FOR PRODUCING A SOCKET OF A PROSTHESIS THEREFROM

[75] Inventors: Lutz Biedermann, VS-Villingen; Markus Piro, Niedereschach, both of Germany

[73] Assignee: Biederamnn Motech GmbH, VS-Schwennigen, Germany

[21] Appl. No.: 09/041,422

[22] Filed: Mar. 12, 1998

[51] Int. Cl.[7] .................................................. A61F 2/60
[52] U.S. Cl. ............................................................ 623/33
[58] Field of Search ................................ 623/33, 32, 22, 623/34, 35, 36, 37

[56] References Cited

U.S. PATENT DOCUMENTS

| | | | |
|---|---|---|---|
| 5,258,036 | 11/1993 | Edenbaum et al. | 623/33 |
| 5,503,543 | 4/1996 | Laghi | 425/2 |
| 5,718,925 | 2/1998 | Kristinsson et al. | 425/2 |

FOREIGN PATENT DOCUMENTS

| | | |
|---|---|---|
| 90 03 681 | 6/1993 | Germany . |
| 195 31 070 | 2/1997 | Germany . |
| WO 95/05792 | 3/1995 | WIPO . |
| WO 96/09077 | 3/1996 | WIPO . |
| WO 96/29033 | 9/1996 | WIPO . |

*Primary Examiner*—V. Millin
*Assistant Examiner*—Alvin Stewart
*Attorney, Agent, or Firm*—George W. Neuner; Dike, Bronstein, Roberts and Cushman, LLP

[57] ABSTRACT

A tubular fabric is provided for forming the shaft of a prosthesis having a predetermined length and one open end, the other end of the shaft being closed for holding a coupling member except for an aperture corresponding to a portion of said coupling member which is inserted therethrough to extend outwardly. The tubular base material is selected to be longer than the length of the shaft of the prosthesis to be formed. By means of a ring the tube is annularly held together from the outside at a predetermined length so as to form a first section starting from the opening. The remaining second section is then folded back over the annular hole onto the first section. To form the shaft of the prosthesis the material is impregnated with a thermoplastic resin.

24 Claims, 3 Drawing Sheets ically corresponds to the diameter of the bolt-shaped portion
TUBULAR FABRIC AND METHOD FOR PRODUCING A SOCKET OF A PROSTHESIS THEREFROM The invention relates to a tubular fabric for forming a socket of a prosthesis receiving a stump of a residual limb of an amputee at one end thereof. The invention further relates to a method for producing such a socket of a prosthesis from said tubular fabric.

U.S. Pat. No. 5,228,164 discloses a set of materials for forming a negative mold of a part of a body.

U.S. Pat. No. 5,507,834 discloses a silicone liner having an open end and a coupling member at the opposite closed end adapted for screwing a bolt there in for connection said liner to a socket of a prosthesis.

OBJECTS OF THE INVENTION

It is an object of the invention to provide an improved prosthesis for a connection to an artificial limb and a method for producing such a prosthesis. It is an object of the invention to provide a tubular fabric for producing, in a simple manner, a prosthesis socket for connection to a mechanical artificial limb part, without having to produce an intermediate form. It is a further object of the invention to provide a method for producing such a socket from said tubular fabric.

SUMMARY OF THE INVENTION

According to the invention a tubular fabric for forming a socket of a prosthesis for connecting a residual limb to a prosthesis is provided. Said socket has a predetermined length and comprises one end having an opening for receiving said residual limb and another end with a bottom which is substantially closed but comprises a through hole for holding a coupling member. The hole corresponds to a portion of said coupling member which is inserted therethrough to extend outwardly therefrom. The tubular fabric is longer than the predetermined length and comprises a first section corresponding to the predetermined length which is held together by a ring like annular holder from the outside and a remaining portion forming a second section which is folded back over the annular holder onto the first section. According to the inventive method for producing such a socket of a prosthesis the tubular fabric is impregnated with a resin, brought over the residual limb and pressed onto the limb from the outside.

BRIEF DESCRIPTION OF THE DRAWINGS

Further advantages, features and objects of the invention will be apparent from the following description of an examplary embodiment with reference to the drawings. In the drawings.

DESCRIPTION OF THE PREFERRED EMBODIMENT

Figure 1:
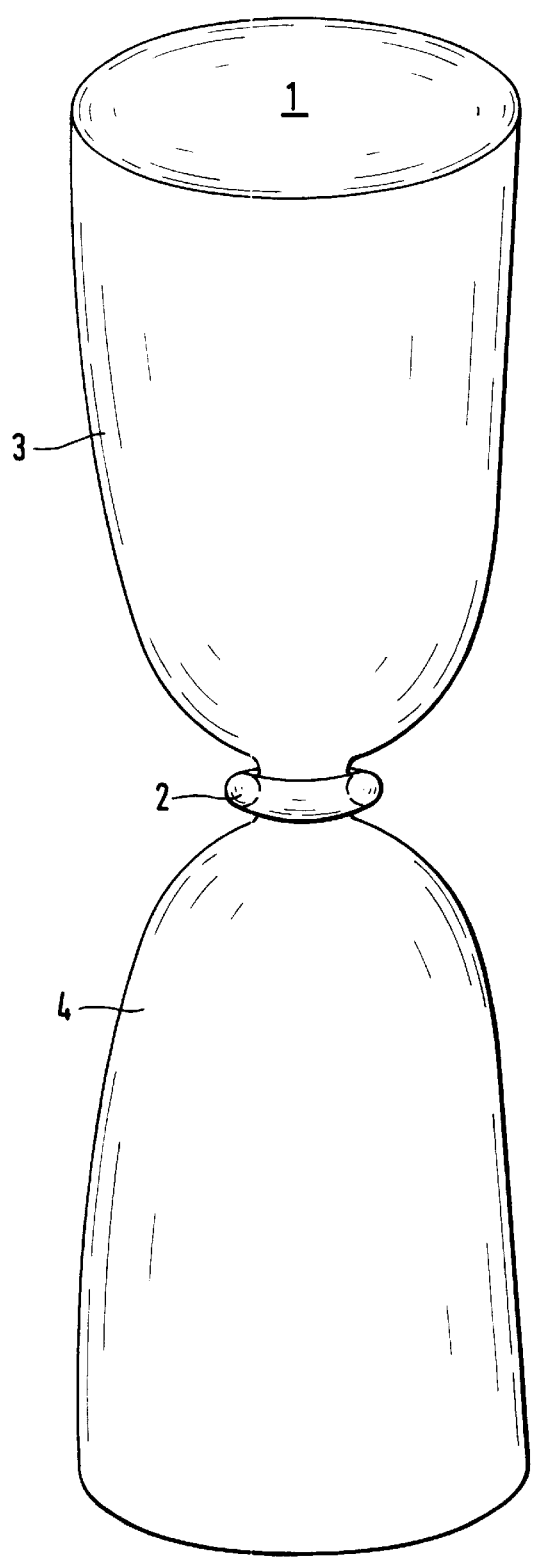
FIG. 1 is a side view of the tubular fabric with the annular holder.
Figure 2:
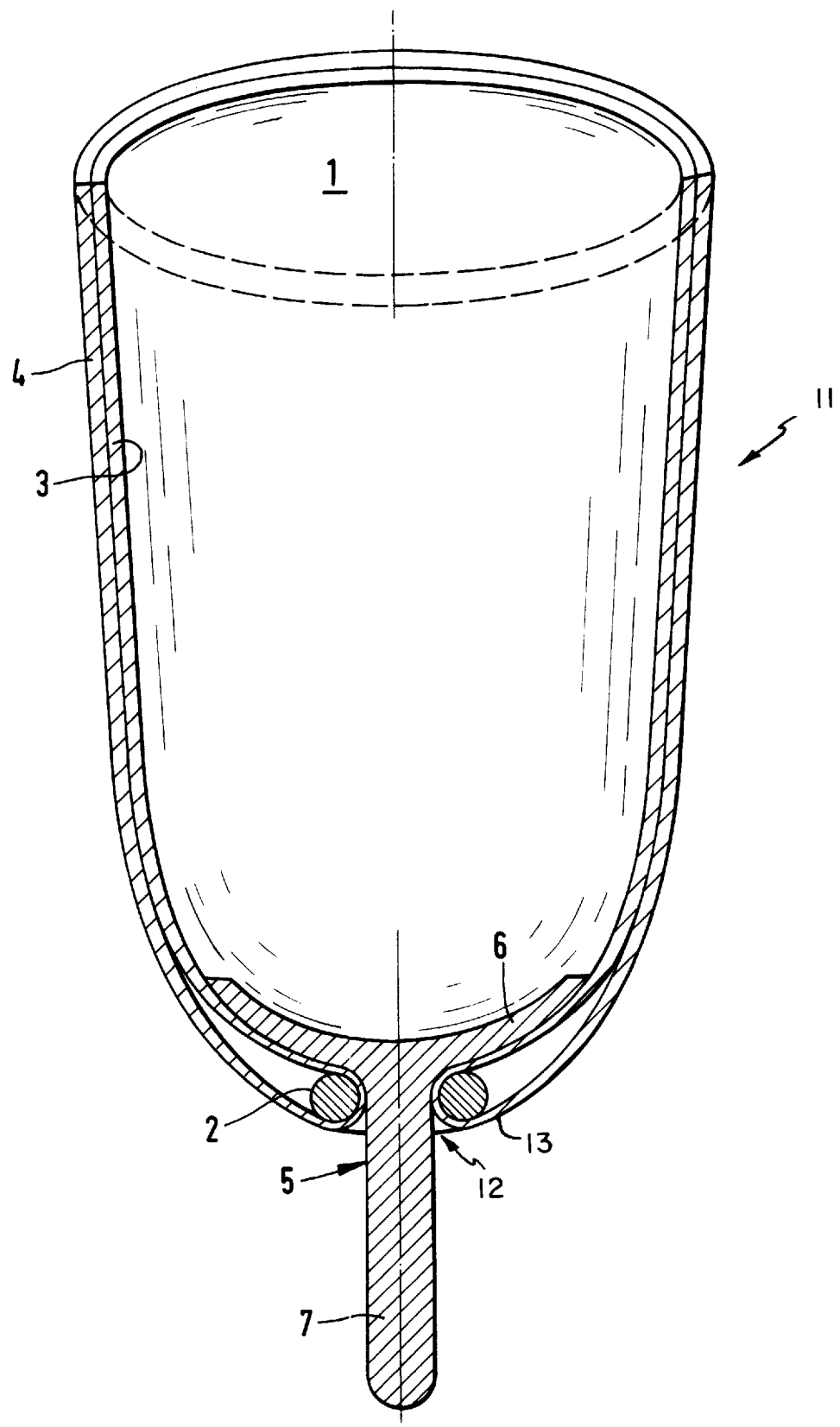
FIG. 2 shows a section through the prosthesis socket with an inserted coupling member.

The base material is a tubular fabric which is knitted from glass fibers. For forming a prosthesis socket a portion of said tubular material corresponding to substantially twice the length of the socket to be formed is cut off. At a predetermined distance from one open end 1 the tube is encircled by a ring 2 and tied up as shown in FIG. 1. The distance from the open end 1 to the ring 2 is selected so that a first portion 3 formed thereby corresponds to the length of the socket to be formed. A second section 4 opposite to said first section 3 is then folded back over said ring 2 and the first section 3 so as to form a douple-walled member 11 shown in FIG. 2. Member 11 comprises a bottom 13 having a central through hole 12.

Figure 3:
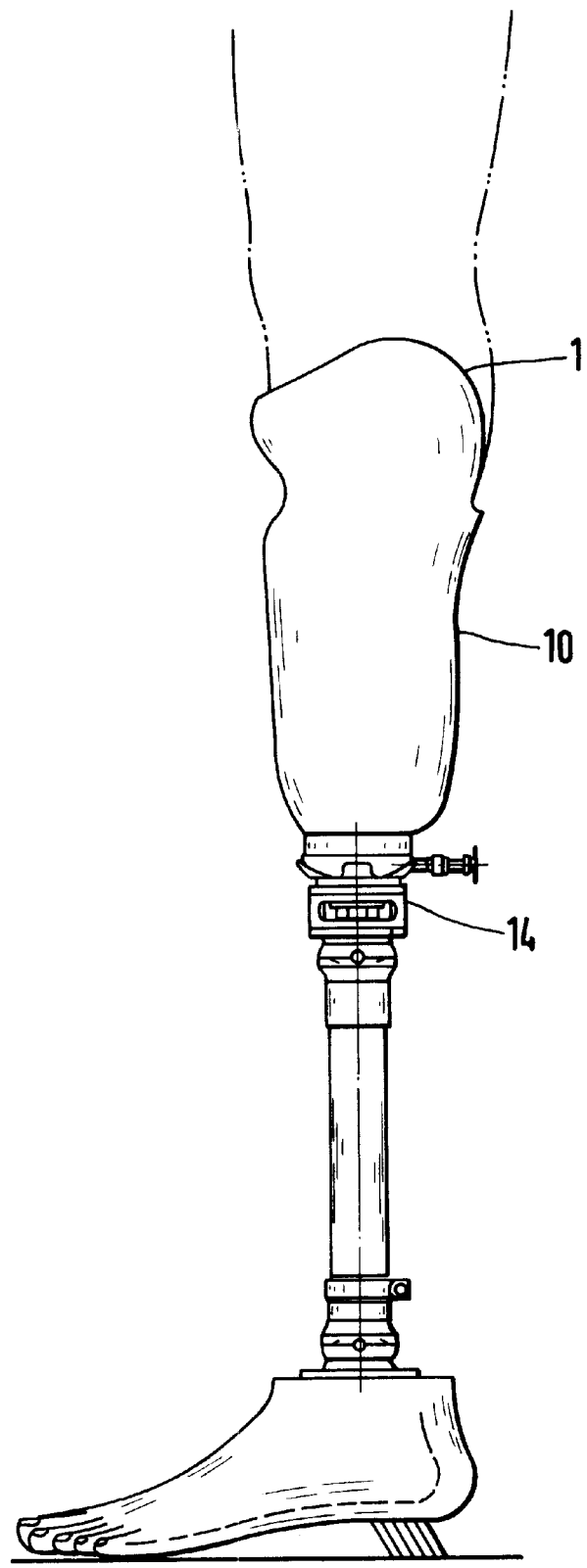
FIG. 3 is a side view of a prosthesis with the said socket.

A coupling member 5 is provided having a plate-shaped portion 6 and a bolt-shaped portion 7. Said member is inserted into the bottom part 13 of member 11 in the manner shown in FIG. 2 by passing through bolt-shaped portion 7 through through hole 12. The diameter of ring 2 is sized so that the bolt-shaped portion 7 just fits through the through hole 12 at bottom 13. The diameter of the through hole 12 formed by the ring 2 by holding the tube together substantially corresponds to the diameter of the bolt-shaped portion 7. In known manner the bolt-shaped portion 7 serves for the connection of the socket 10 with a prosthesis as shown in FIG. 3. The plate-shaped portion 6 is formed to smoothly fit the bottom 13 of the closed end of member 11 and to support the bolt-shaped portion 7.

After preparing the member 11 including coupling member 5 as described the fabric is impregnated with a resin. The resin is a material with self-hardening properties which preferably can be activated using water and generates little heat when hardening. A preferred example for such a resin is polyurethane resin. Preferably, the resin should exhibit thermoplastic properties when hardened.

For forming the prosthesis socket said prepared fabric is dipped into activating water and then pulled over a residual limb which may have been covered with a liner. The wall of the member 11 is then pressed against the surface of the residual limb to adapt the form of member 11 to the residual limb. The edge may also be folded over, if desired, in a manner to make it comfortable to wear. The upper free edge of the finally formed member is then cut to size after hardening.

If pressure marks show up when wearing the socket it can be reformed by warming up the wall of member 11 at the relevant parts.

In the above embodiment the fabric is made of glass fibers. According to a modified embodiment the fabric is made of a combination of glass fibers with others reinforcing fibers such as carbon or kevlar aramid fibers.

Although the invention has been described with reference to a specific example embodiment it is to be understood that it is intended to cover all modifications and equivalents within the spirit and scope of the appended claims.

What is claimed is:

1. A prosthesis socket for receiving a residual limb, said socket comprising:

a length of tubular fabric having an open end for receiving the residual limb, an annular member having an inner diameter and positioned around said tubular fabric at a predetermined distance from said open end, and a coupling member comprising a plate portion having a diameter greater than the inner diameter of said annular member and a bolt portion for attaching a prosthesis thereto for attaching said prosthesis to the socket, said length of tubular fabric being greater than said predetermined distance and having a first section equal in length to said predetermined distance and a second section extending from said annular member away from said open end, said annular member forming a through hole into which said bolt portion is inserted from said open end, wherein said second section is folded back over said annular member onto said first section to provide at least a portion of said socket having double thickness of tubular fabric.

2. A prosthesis socket in accord with claim 1, wherein said second section substantially corresponds in length to said first section.

3. A prosthesis socket in accord with claim 1, wherein the fabric comprises glass fibers.

4. A prosthesis socket in accord with claim 3, wherein the fabric further comprises additional reinforcing fibers.

5. A prosthesis socket in accord with claim 4, wherein the reinforcing fibers are carbon or aramid fibers.

6. A prosthesis socket in accord with claim 1, wherein the fabric is impregnated with a self-hardening resin.

7. A prosthesis socket in accord with claim 6, wherein the self-hardening resin can be water activated.

8. A prosthesis socket in accord with claim 6, wherein the self-hardening resin forms a thermoplastic material.

9. A method for making a prosthesis socket for receiving a residual limb, said method comprising:

providing a length of tubular fabric having an open end for receiving the residual limb, providing an annular member having an inner diameter and positioning it around said tubular fabric at a predetermined distance from said open end, providing a coupling member comprising a plate portion having a diameter greater than the inner diameter of said annular member and a bolt portion for attaching a prosthesis thereto for attaching said prosthesis to the socket, said length of tubular fabric being greater than said predetermined distance and having a first section equal in length to said predetermined distance and a second section extending from said annular member away from said open end, inserting said bolt portion of said coupling member into the through hole from said open end, and folding back said second section over said annular member onto said first section to provide at least a portion of said socket having double thickness of tubular fabric.

10. A method for making a prosthesis socket in accord with claim 9, wherein said second section substantially corresponds in length to said first section.

11. A method for making a prosthesis socket in accord with claim 9, wherein the fabric comprises glass fibers.

12. A method for making a prosthesis socket in accord with claim 11, wherein the fabric further comprises additional reinforcing fibers.

13. A method for making a prosthesis socket in accord with claim 12, wherein the reinforcing fibers are carbon or aramid fibers.

14. A method for making a prosthesis socket in accord with claim 9, further comprising impregnating the fabric with a self-hardening resin.

15. A method for making a prosthesis socket in accord with claim 14, further comprising activating the self-hardening resin with water.

16. A method for making a prosthesis socket in accord with claim 14, further comprising forming a thermoplastic material with the self-hardening resin.

17. A combination for assembling a prosthesis socket for receiving a residual limb, said combination comprising:

a length of tubular fabric having an open end for receiving the residual limb, an annular member having an inner diameter and positioned around said tubular fabric at a predetermined distance from said open end, and a coupling member comprising a plate portion having a diameter greater than the inner diameter of said annular member and a bolt portion for attaching a prosthesis thereto for attaching said prosthesis to the socket, said length of tubular fabric being greater than said predetermined distance and having a first section equal in length to said predetermined distance and a second section extending from said annular member away from said open end, said annular member providing a through hole into which said bolt portion can be inserted from said open end.

18. A combination in accord with claim 17, wherein the fabric comprises glass fibers.

19. A combination in accord with claim 18, wherein the fabric further comprises additional reinforcing fibers.

20. A combination in accord with claim 19, wherein the reinforcing fibers are carbon or aramid fibers.

21. A combination in accord with claim 17, wherein the fabric is impregnated with a self-hardening resin.

22. A combination in accord with claim 21, wherein the self-hardening resin can be water activated.

23. A combination in accord with claim 21, wherein the self-hardening resin forms a thermoplastic material.

24. A method for making a prosthesis socket for receiving a residual limb, said method comprising:

providing a length of tubular fabric having an open end for receiving the residual limb, providing an annular member having an inner diameter and positioning it around said tubular fabric at a predetermined distance from said open end thereby forming a through hole, providing a coupling member comprising a plate portion having a diameter greater than the inner diameter of said annular member and a bolt portion for attaching a prosthesis thereto for attaching said prosthesis to the socket, said length of tubular fabric being greater than said predetermined distance and having a first section equal in length to said predetermined distance and a second section extending from said annular member away from said open end, folding back said second section over said annular member onto said first section to provide at least a portion of said socket having double thickness of tubular fabric, and inserting said bolt portion of said coupling member into the through hole from said open end to position the plate portion adjacent the annular member for attaching the prosthesis thereto.

* * * * *

UNITED STATES PATENT AND TRADEMARK OFFICE
CERTIFICATE OF CORRECTION

PATENT NO. : 6,156,071
DATED : December 5, 2000
INVENTOR(S) : Biedermann et al.

It is certified that error appears in the above-identified patent and that said Letters Patent is hereby corrected as shown below:

<u>Title page,</u>
Insert item:
-- [30] Foreign Application Priority Data
March 12, 1997    (DE)    197 10 230.1 --

Signed and Sealed this

Thirteenth Day of July, 2004

JON W. DUDAS
*Acting Director of the United States Patent and Trademark Office*